United States Patent
Ullmann

(10) Patent No.: US 12,220,141 B2
(45) Date of Patent: Feb. 11, 2025

(54) CATHETER SYSTEM WITH INDEPENDENTLY CONTROLLABLE BUBBLE AND ARC GENERATION

(71) Applicant: Shockwave Medical, Inc., Santa Clara, CA (US)

(72) Inventor: Jens Ullmann, San Jose, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/216,084

(22) Filed: Jun. 29, 2023

(65) Prior Publication Data
US 2025/0000532 A1      Jan. 2, 2025

(51) Int. Cl.
*A61B 17/22* (2006.01)
*A61B 17/00* (2006.01)

(52) U.S. Cl.
CPC ............ *A61B 17/22022* (2013.01); *A61B 2017/00181* (2013.01); *A61B 2017/00194* (2013.01); *A61B 2017/22025* (2013.01); *A61B 2017/22038* (2013.01); *A61B 2017/22064* (2013.01); *A61B 2017/22089* (2013.01)

(58) Field of Classification Search
CPC .......... A61B 2017/00181; A61B 2017/00194; A61B 2017/22025; A61B 2017/22038; A61B 2017/22064; A61B 2017/22089; A61B 2017/22091; A61B 2017/22051
See application file for complete search history.

(56) References Cited

U.S. PATENT DOCUMENTS

| | | |
|---|---|---|
| 2,916,647 A | 12/1959 | George |
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

International Search Report and Written Opinion received for PCT Patent Application No. PCT/US2023/071702, mailed on Mar. 25, 2024, 6 pages.

*Primary Examiner* — Brigid K Byrd
(74) *Attorney, Agent, or Firm* — Morrison & Foerster LLP

(57) ABSTRACT

Described herein are systems and methods for implementing a power source for a shock wave catheter system, the power source including two separate voltage sources: a bubble generation voltage source and an arc generation voltage source. In one or more examples, the power source can be configured such that the bubble generation voltage source provides a lower voltage to a pair of electrodes of the shock wave catheter system. The lower voltage can be configured to induce electrolysis of a fluid that surrounds the pair of electrodes of the shock wave catheter system for generating and growing a bubble. Once a bubble has formed, the arc generation voltage source can then be engaged to provide a high-voltage electrical pulse to the electrodes of the shock wave catheter system, thereby generating an arc (i.e., spark) across the electrodes.

23 Claims, 14 Drawing Sheets

(56) References Cited

U.S. PATENT DOCUMENTS

| | | |
|---|---|---|
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,101,682 A * | 4/1992 | Radisch, Jr. ........ A61M 25/005 138/143 |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,855,904 B2 | 12/2010 | Kirbie et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |

(56) References Cited

U.S. PATENT DOCUMENTS

| | | |
|---|---|---|
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0182397 A1* | 8/2005 | Ryan ............... A61B 18/1492 606/29 |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0058782 A1 | 3/2006 | Truckai et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1* | 1/2007 | Schultheiss ...... A61B 17/22004 601/4 |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 1/2010 | Hawkins et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0052145 A1* | 2/2014 | Adams ................. A61B 17/225 137/13 |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2019/0117242 A1 | 4/2019 | Lawinger et al. |
| 2019/0388110 A1 | 12/2019 | Nguyen |
| 2021/0085347 A1 | 3/2021 | Phan et al. |
| 2021/0085383 A1 | 3/2021 | Vo et al. |
| 2021/0338258 A1 | 11/2021 | Hawkins et al. |
| 2021/0338259 A1* | 11/2021 | Novak ............... A61B 17/2258 |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 111969882 A | 11/2020 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2011520248 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011524203 A | 9/2011 |
| JP | 2011528963 A | 12/2011 |
| JP | 2012505050 A | 3/2012 |
| JP | 2012508042 A | 4/2012 |

(56) References Cited

FOREIGN PATENT DOCUMENTS

| | | |
|---|---|---|
| JP | 2015525657 A | 9/2015 |
| JP | 2015528327 A | 9/2015 |
| JP | 6029828 B2 | 11/2016 |
| JP | 6081510 B2 | 2/2017 |
| KR | 20220045569 A | 4/2022 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |
| WO | WO-2021026538 A1 | 2/2021 |

\* cited by examiner

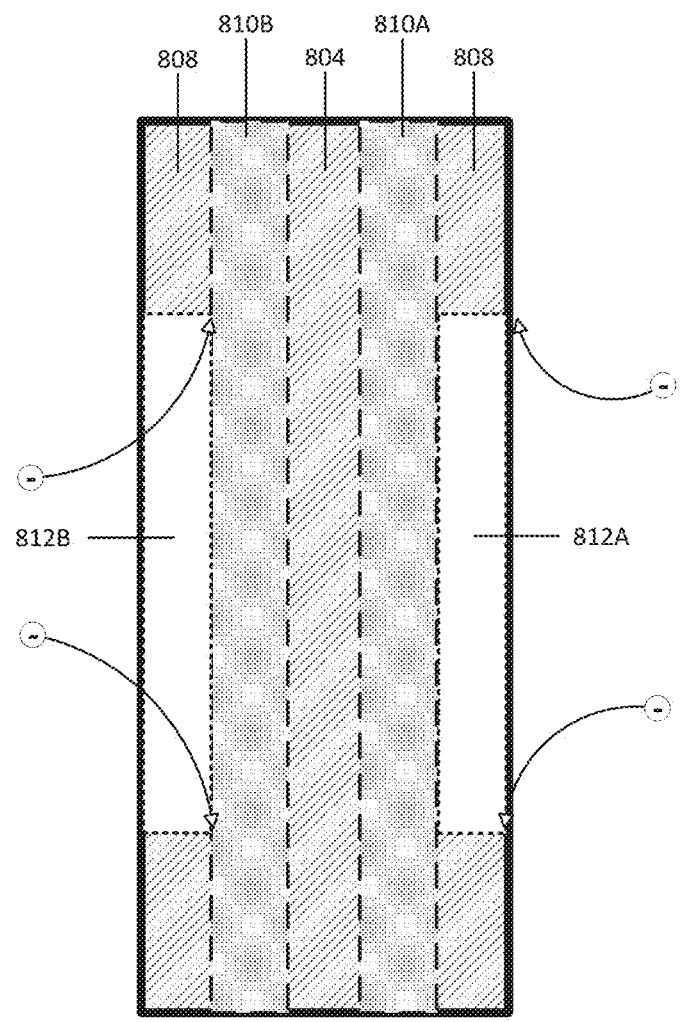

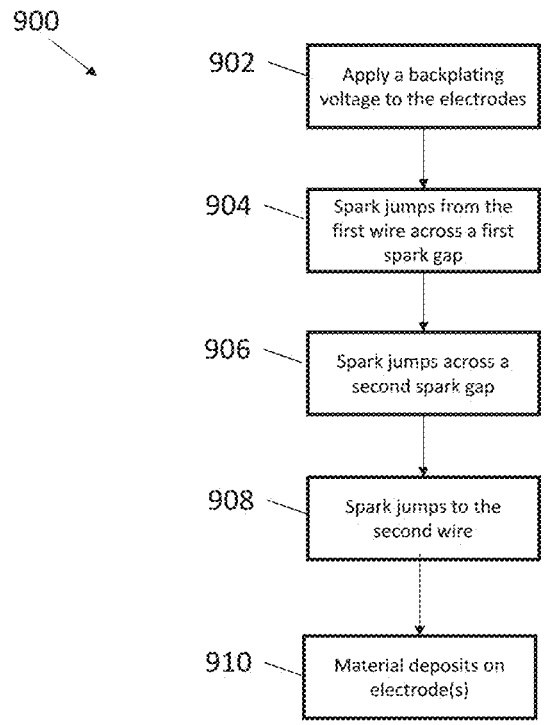

CATHETER SYSTEM WITH INDEPENDENTLY CONTROLLABLE BUBBLE AND ARC GENERATION

FIELD OF THE DISCLOSURE

The present disclosure relates generally to medical devices and associated methods, and more specifically, to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. or laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel or non-calcified plaque.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion, but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

Efforts have been made to improve the delivery of shock waves in these devices. For instance, forward-biased designs, such as the designs found in U.S. Pat. No. 10,966, 737 and U.S. Publication No. 2019/0388110, both of which are incorporated herein by reference, direct shock waves in a generally forward direction (e.g., distally from the distal end of a catheter) to break up tighter and harder-to-cross occlusions in vasculature. Other catheter devices have been designed to include arrays of low-profile electrode assemblies that reduce the crossing profile of the catheter and allow the catheter to more easily navigate calcified vessels to deliver shock waves in more severely occluded regions of vasculature. For instance, U.S. Pat. Nos. 8,888,788, and 10,709,462 and U.S. Publication No. 2021/0085347, each of which is incorporated herein by reference, provide examples of low-profile electrode assemblies. Such forward-biased and low-profile designs are particularly useful when an artery is totally or partially occluded, for example, with thrombus, plaque, fibrous plaque, and/or calcium deposits. When treating such conditions, a physician must first cross the occlusion (e.g., pass through the occluded area), and then feed the angioplasty balloon and/or other tools down the artery to the blockage to perform the desired procedure. In some instances, however, such as the case of a chronic total occlusion ("CTO"), the occlusion may be so tight and solid that it is difficult to cross the treatment device into the true lumen of the distal vessel. Some physicians may implement atherectomy procedures (e.g., laser-based, mechanically cutting or shaving, mechanically rotating devices, etc.) to form a channel in a CTO in combination with an angioplasty balloon treatment, but many atherectomy devices and systems carry a higher risk of vessel perforation or vessel dissection as compared with a basic angioplasty balloon catheters.

Shock wave emitters include a pair of electrodes coupled to a voltage source. Application of a sufficiently high voltage pulse across the pair of electrodes can generate a momentary electrical arc across the electrodes that causes the rapid expansion and collapse of a bubble, which generates a shock wave that can break up calcified lesions in vasculature. It is known to apply a relatively low voltage to the electrode pair to generate and grow a bubble, and then apply a relatively high voltage pulse to generate a momentary arc that causes the bubble to rapidly expand and collapse, generating the shock wave.

The low voltage used to prime an aqueous environment or generate one or more bubbles on an electrode and the high voltage used to generate the electrical arc across the electrodes to form the shock wave can be supplied by the same power source. However, using the same power source for multiple purposes (e.g., bubble creation and arc creation) can lead to an inefficient use of energy and also require a larger voltage source that can lead to an increased footprint of the power source. Furthermore, using a single power source for both bubble creation and arc creation means that bubble creation and arc creation are not independently controllable since the power source is optimized for the main function of arc creation, making the two processes dependent on one another.

SUMMARY

Described herein are systems and methods for implementing a power source for a shock wave catheter system, the power source including two separate voltage sources: a bubble generation voltage source and an arc generation voltage source. In one or more examples, the power source can be configured such that the bubble generation voltage source provides a lower voltage to a pair of electrodes of the shock wave catheter system. The lower voltage can be configured to induce electrolysis of a fluid that surrounds the pair of electrodes of the shock wave catheter system for generating and growing a bubble. Once a bubble has formed, the arc generation voltage source can then be engaged to provide a high-voltage electrical pulse to the electrodes of the shock wave catheter system, thereby generating an arc (i.e., spark) across the electrodes.

In one or more examples, the bubble generation voltage source and the arc generation voltage source can be placed together in one or more circuits, such as in a single circuit, and configured such that the voltage sources are independently controllable. In one or more examples, both voltage sources can be electrically separated from one another using one or more electrical components, such as inductors and diodes, so that the operation of one voltage source does not impact the operation of the other voltage source.

Described here are methods for generating a shock wave in a shock wave catheter system. The method comprises applying a first voltage, using a first voltage source, to one or more electrodes of the shock wave catheter system to prime an aqueous environment or generate one or more bubbles in a fluid surrounding the one or more electrodes; and applying a second voltage, using a second voltage source, to the one or more electrodes to generate an electrical arc at the one or more electrodes, wherein the first voltage source and the second voltage source are independently controllable.

In some variations, the method comprises: selectively electrically coupling or decoupling the first voltage source or the second voltage source with the one or more electrodes.

In some variations, the method comprises: electrically separating the first voltage source from the second voltage source.

In some variations, the electrically separating comprises restricting current flow between the first voltage source and the second voltage source.

In some variations, the method comprises: receiving an external input corresponding to a user operating a button; and generating one or more signals to control a first switch or a second switch of the shock wave catheter system based on the external input.

In some variations, the method comprises: operating the shock wave catheter system in a bubble generation mode, comprising: closing a first switch to electrically couple the first voltage source with the one or more electrodes; and opening a second switch to electrically decouple the second voltage source from the one or more electrodes.

In some variations, the method comprises: operating the shock wave catheter system in an arc generation mode, comprising: closing a second switch to electrically couple the second voltage source with the one or more electrodes.

In some variations, the method comprises: determining whether a bubble has been formed at the one or more electrodes; and in accordance with the bubble having been formed, operating the shock wave catheter system in an arc generation mode.

In some variations, the determining whether a bubble has been formed comprises determining whether the shock wave catheter system has operated in a bubble generation mode for a threshold amount of time.

In some variations, the determining whether a bubble has been formed comprises determining whether an amount of current flowing from the first voltage source to the one or more electrodes meets a threshold amount of current.

In some variations, the amount of current flowing meeting the threshold amount of current comprises the amount of current flowing being less than 100 µA.

In some variations, the method comprises: determining whether an amount of current flowing from the second voltage source to the one or more electrodes meets a threshold amount of current; and in accordance with the amount of current flowing meeting the threshold amount of current, terminating operation of the shock wave catheter system in an arc generation mode.

In some variations, the amount of current flowing meeting the threshold amount of current comprises the amount of current flowing being greater than 50 A.

In some variations, the method comprises: operating the shock wave catheter system in a bubble generation mode; and operating the shock wave catheter system in an arc generation mode, wherein a period of time for operating in the bubble generation mode is longer than a period of time for operating in the arc generation mode.

In some variations, the applied first voltage is less than the applied second voltage.

In some variations, the applied first voltage is from 50 to 250 volts.

In some variations, the applied second voltage is from 2,000 to 10,000 volts.

In some variations, the first voltage is applied across the one or more electrodes of the shock wave catheter system.

In some variations, the second voltage is applied across the one or more electrodes of the shock wave catheter system.

In some variations, the method comprises: applying a third voltage to the one or more electrodes of the shock wave catheter system to cause metal to be deposited on the one or more electrodes.

In some variations, the applied third voltage is less than the applied first voltage.

In some variations, the third voltage is applied when the one or more electrodes is surrounded by a second fluid, wherein the second fluid is compatible with a backplating operation.

In some variations, the fluid surrounding the one or more electrodes comprises a fluid compatible with backplating and a fluid compatible with bubble generation.

In some variations, a volume of the fluid surrounding the one or more electrodes comprises 10-25% of the fluid compatible with backplating and 75-90% of the fluid compatible with bubble generation.

In some variations, the one or more electrodes are included in an electrode pair, and the first voltage and the second voltage are applied to electrodes of the electrode pair.

Described here are pulse generators for shock wave catheter systems. A pulse generator comprises: a first voltage source configured to apply a first voltage at one or more electrodes of the shock wave catheter system to generate one or more bubbles in a fluid surrounding the one or more electrodes; a second voltage source configured to apply a second voltage at the one or more electrodes of the shock wave catheter system to generate an electrical arc at the one or more electrodes; and one or more separation components configured to electrically separate the first voltage source from the second voltage source, wherein the first voltage source and the second voltage are independently controllable.

In some variations, the pulse generator comprises: a first switch, when closed, configured to electrically couple the first voltage source with the one or more electrodes and, when open, configured to electrically decouple the first voltage source from the one or more electrodes.

In some variations, the pulse generator comprises: a second switch, when closed, configured to electrically couple the second voltage source with the one or more electrodes and, when open, electrically decouple the second voltage source from the one or more electrodes.

In some variations, the pulse generator comprises: a first switch coupled to the first voltage source and a second switch coupled to the second voltage source, wherein the first switch and the second switch are insulated-gate bipolar transition switches.

In some variations, the pulse generator comprises: one or more controllers coupled to a first switch or a second switch, wherein the one or more controllers are configured to open and close the first switch or the second switch based on an external input.

In some variations, the external input comprises a user operating a button, and wherein the one or more controllers are configured to determine that the button has been operated and generate one or more signals to the first switch and the second switches to independently open and close the first switch and the second switch.

In some variations, the one or more separation components comprise an inductor placed between the first voltage source and the second voltage source and configured to restrict current flow between the first voltage source and the second voltage source.

In some variations, the one or more separation components comprise a diode placed in parallel with the first and second voltage sources and configured to restrict current flow between the first voltage source and the second voltage source.

In some variations, the first voltage source is in parallel and in opposite polarity to the second voltage source.

In some variations, the pulse generator is configured to operate in a bubble generation mode, wherein during the bubble generation mode, a first switch is closed to electrically couple the first voltage source to the one or more electrodes, and a second switch is open to electrically decouple the second voltage source from the one or more electrodes.

In some variations, the pulse generator is configured to operate in an arc generation mode, wherein during the arc generation mode, a second switch is closed to electrically couple the second voltage to the one or more electrodes.

In some variations, the arc generation mode is initiated upon a determination that a bubble has been formed at the one or more electrodes.

In some variations, the determination that the bubble has formed comprises a determination that the first voltage source has operated in the bubble generation mode for a threshold amount of time.

In some variations, the determination that the bubble has formed comprises a determination that the first voltage source has delivered a threshold amount of current to the one or more electrodes while operating in the bubble generation mode.

In some variations, the first voltage applied to the one or more electrodes is less than the second voltage applied to the one or more electrodes.

In some variations, the first voltage applied to the one or more electrodes by the first voltage source is from 50 to 250 volts.

In some variations, the second voltage applied to the one or more electrodes by the second voltage source is from 2,000 to 10,000 volts.

In some variations, the first voltage is applied across the one or more electrodes of the shock wave catheter system.

In some variations, the second voltage is applied across the one or more electrodes of the shock wave catheter system.

In some variations, the pulse generator comprises: a third voltage source configured to apply a third voltage at the one or more electrodes of the shock wave catheter system to cause metal to be deposited on the one or more electrodes.

In some variations, the applied third voltage is less than the applied first voltage.

In some variations, the third voltage is applied when the one or more electrodes is surrounded by a second fluid, wherein the second fluid is compatible with a backplating operation.

In some variations, the fluid surrounding the one or more electrodes comprises a fluid compatible with backplating and a fluid compatible with bubble generation.

In some variations, a volume of the fluid surrounding the one or more electrodes comprises 10-25% of the fluid compatible with backplating and 75-90% of the fluid compatible with bubble generation.

Described here are systems for generating voltages at one or more electrodes of shock wave catheter systems. A system comprises: a pulse generator, the pulse generator comprising: a first voltage source configured to apply a first voltage at one or more electrodes of the shock wave catheter system to generate one or more bubbles in a fluid surrounding the one or more electrodes, a first switch, when closed, configured to electrically couple the first voltage source with the one or more electrodes, a second voltage source configured to apply a second voltage at the one or more electrodes of the shock wave catheter system, wherein the second voltage is larger than the first voltage, and wherein the second voltage is configured to induce electrical arcing at the one or more electrodes, a second switch, when closed, configured to electrically couple the second voltage source with the one or more electrodes, and one or more separation components, wherein the one or more separation components are configured to electrically separate the first voltage source from the second voltage source such that the first voltage source and the second voltage are independently controllable; and memory and one or more processors, wherein the memory stores one or more programs that when executed by the one or more processors, cause the one or more processors to: receive an external indicator to generate a shock wave, operate the pulse generator to generate the first voltage at the one or more electrodes so as to generate the one or more bubbles in the fluid, and operate the pulse generator to generate the second voltage at the one or more electrodes so as to generate an electrical arc at the one or more electrodes.

BRIEF DESCRIPTION OF THE FIGURES

Illustrative aspects of the present disclosure are described in detail below with reference to the following drawing figures. It is intended that that embodiments and figures disclosed herein are to be considered illustrative rather than restrictive.

FIGS. 8B and 8C illustrate cross-sectional views taken along A-A of the example electrode assembly of FIG. 8A, according to examples of the disclosure.

FIG. 9A illustrates an exemplary process for a backplating operation when a positive polarity (FIG. 8B) is applied for the backplating operation, according to examples of the disclosure.

DETAILED DESCRIPTION

Figure 1:
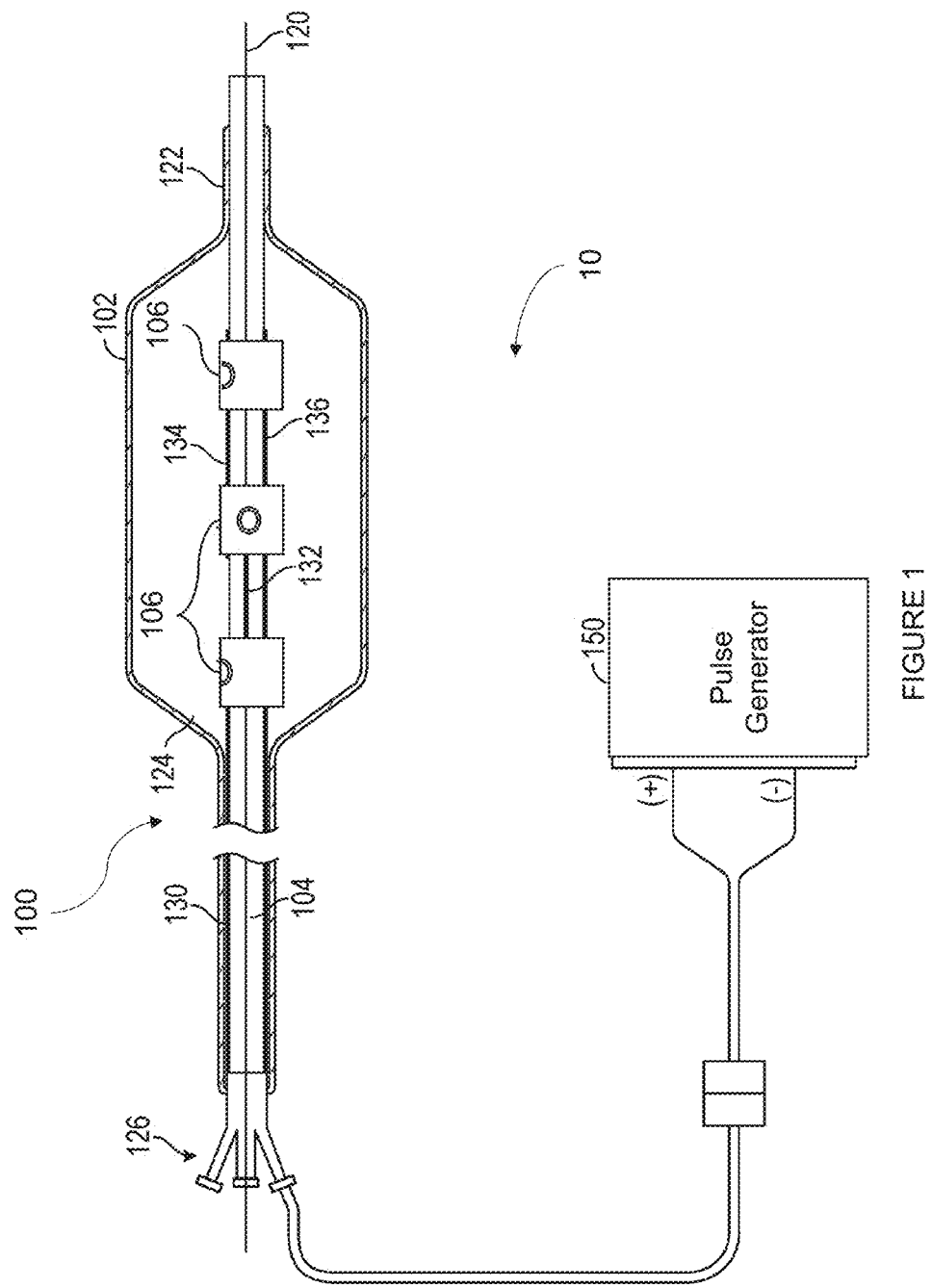
FIG. 1 illustrates a simplified view of a shock wave catheter system, according to examples of the disclosure.

The following description is presented to enable a person of ordinary skill in the art to make and use the various embodiments disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but rather are to be accorded the scope consistent with the claims.

Described herein are systems and methods for implementing a power source for a shock wave catheter system. The power source includes separate voltage sources: a bubble generation voltage source and an arc generation voltage source. The bubble generation voltage source can provide a lower voltage to a pair of electrodes of a shock wave catheter system. The lower voltage can be configured to induce electrolysis of a fluid that surrounds the pair of electrodes of the shock wave catheter system for generating and growing a bubble. Once a bubble has formed, the arc generation voltage source can then be engaged to provide a high-voltage electrical pulse to the electrodes of the shock wave catheter system, thereby generating an electrical arc (i.e., spark) across the electrodes. In one or more examples, the bubble generation voltage source and the arc generation voltage source can be placed together in a single circuit but configured such that they are independently controllable. In one or more examples, both voltage sources can be electrically separated from one another using one or more electrical components, such as inductors and diodes, so that the operation of one voltage source does not impact the operation of the other voltage source.

As used herein, the term "electrode" refers to an electrically conducting element (e.g., made of metal) that receives electrical current and subsequently releases the electrical current to another electrically conducting element. In the context of the present disclosure, electrodes are often positioned adjacent to each other, such as in an arrangement of an inner electrode and an outer electrode. Accordingly, as used herein, the term "electrode pair" refers to two electrodes that are positioned adjacent to each other such that application of a sufficiently high voltage to the electrode pair may cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the terms "shock wave emitter" and "shock wave generator" broadly refer to the region of an electrode assembly where the current travels across the electrode pair, generating a shock wave. In the context of the present disclosure, the term "emitter" broadly refers to the region of an electrode assembly where the current transmits across the electrode pair, generating a shock wave. The term "emitter sheath" refers to a sheath of conductive material that may form one or more electrodes of one or more electrode pairs, thereby forming a location of one or more emitters. The term "emitter band" refers to a band of conductive material that may form one or more electrodes of one or more electrode pairs, thereby forming a location of one or more emitters.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave, and vice versa. Accordingly, numerical designators of various elements and features are not intended to limit the disclosure and may be modified and interchanged without departing from the subject invention.

FIG. 1 illustrates a simplified view of a shock wave catheter system, according to examples of the disclosure. The system 100 of FIG. 1 is meant to provide an exemplary context to the pulse generator described below and should not be seen as limiting to the disclosure. The systems and methods described below could be applied to various shock wave catheter systems that may be implemented in a manner that is different from the system 100 of FIG. 1.

In one or more examples, the shock wave catheter 100 can include an elongated tube 104 and a balloon 102. In the example of system 100, the balloon 102 wraps circumferentially around a portion of the elongated tube 104 in a sealed configuration via, for example, a seal 122. The balloon 102 forms an annular channel 124 around the elongated tube 104 through which a conductive fluid, such as saline, may be admitted to the balloon 102 via fill ports 126. The balloon 102 can be filled with a conductive fluid such that the balloon 102 can be inflated and be in apposition along, or in contact with, the walls of a body lumen (such as the walls of an artery proximate to a calcified lesion). Unlike traditional angioplasty balloons which are often inflated to a pressure where the exterior of such balloons is frictionally fit to the vessel walls, the balloon 102 can be inflated to a relatively lower pressure sufficient to position the exterior of balloon 102 at a target location within a body lumen, thereby forming gentle contact with the walls of a body lumen. In one or more examples, the conductive fluid may also contain an x-ray contrast fluid to permit fluoroscopic viewing of the catheter by a surgeon during use.

In one or more examples, the elongated tube 104 can include a number of longitudinal grooves or channels configured for retaining wires, fiber optic cables, and/or inner electrodes. The elongated tube 104, for instance, can include a plurality of (e.g., four) grooves that extend along the length of the elongated tube 104 for receiving insulated wires 130, 132, 134, and 136 (which may be fiber optic cables in other embodiments). The distal ends of the insulated wires can be coupled to a number of shock wave generators 106 located within the balloon 102 and circumferentially wrapped around the elongated tube 104. Each of the shock wave generators 106 includes at least one electrode pair, with the electrodes of each pair spaced apart from one another by a distance, creating a gap. The gap (distance between the electrodes of an electrode pair) may vary according to the magnitude of the high voltage pulse applied to the shock wave generator 106. For example, a gap of about 0.004 inches (101.6 μm) to about 0.006 inches (152.4 μm) may be effective for shock wave generation using voltage pulses of about 3,000 V.

The system 10 includes a pulse generator 150 that is coupled to the proximal ends of the insulated wire 130 and the insulated wire 136. The insulated wires provide one or more voltages to the shock wave generators 106. As a voltage is applied across the insulated wires by the pulse generator 150, each pulse initially ionizes the conductive fluid inside the balloon 102 to generate small gas bubbles around the shock wave generators 106 that insulate the electrodes. Subsequently, a plasma arc forms across a gap between the electrodes of the electrode pairs, generating a low impedance path where current flows freely. The heat from the plasma arc heats the conductive fluid to generate a rapidly expanding vapor bubble. The expansion and collapse of the vapor bubble generates a shock wave that radiates outwardly though the balloon 102 and then through the blood to the calcified lesion proximate to the balloon 102.

As shown in FIG. 1, the catheter 100 has three shock wave generators 106 where an emitter band constitutes the outer electrode for each shock wave generator. However, this is provided for example only and should not be construed as limiting in any manner as the catheter 100 could include one shock wave generator, two shock wave generators, or more than three shock wave generators. When the catheter 100 includes multiple shock wave generators, the shock wave generators 106 may be located within close proximity to one another such that the shock waves generators 106 can constructively interfere with one another. For instance, the shock wave generators 106 can be spaced apart longitudinally less than 6 mm (0.2362 inches) from one another, such as spaced apart by a distance between 1 mm (0.0393 inches) and 4 mm (0.1574 inches) (or at increments of distance therebetween), such that the shock waves generated at a first shock wave generator and a second shock wave generator constructively interfere to produce a combined shock wave. This distance that the shock wave generators 106 are spaced apart can be measured either from edge-to-edge or from centerpoint-to-centerpoint of two proximate or adjacent shock wave generators 106.

The elongated tube 104 includes a lumen through which a guidewire 120 is inserted. In operation, a physician uses the guidewire 120 to guide the elongated tube 104 into position proximate to a calcified lesion in a body lumen. Once positioned, the pulse generator 150 is used to deliver a series of pulses to generate a series of shock waves at the shock wave generators 106 within the balloon 102 and within the body lumen being treated. The magnitude of the shock waves can be controlled by controlling the magnitude of the pulsed voltage, the current, the duration, and the repetition rate of the voltage supplied by the pulse generator 150. The physician may start with low energy shock waves and increase the energy as needed to crack calcified plaques. Such shock waves may travel through the conductive fluid within the balloon 102, through the blood to the calcified lesion where the energy may break apart or crack the hardened plaques.

In one or more examples, the pulse generator 150 can generate voltages at the electrodes for multiple distinct and specific purposes. First, the pulse generator can be configured to generate and apply a first voltage at the electrodes for priming an aqueous environment and/or generating one or more bubbles in the fluid. In some examples, the first voltage is applied across the electrodes. Second, the pulse generator can be also configured to generate and apply a second voltage at the electrodes for generating an arc at the electrodes. In some examples, the second voltage is applied across the electrodes. The arc may generate the shock wave that is used to break apart calcified lesion or other abnormality in the body lumen. In one or more examples, the two voltages can be generated by the same voltage source, but as discussed in detail below, having a single voltage source generate both voltages (e.g., a first voltage for generating a bubble, and a second voltage for generating an arc) can be inefficient and lead to a device with an unnecessarily large footprint/size for the voltage source.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

Figure 2A:
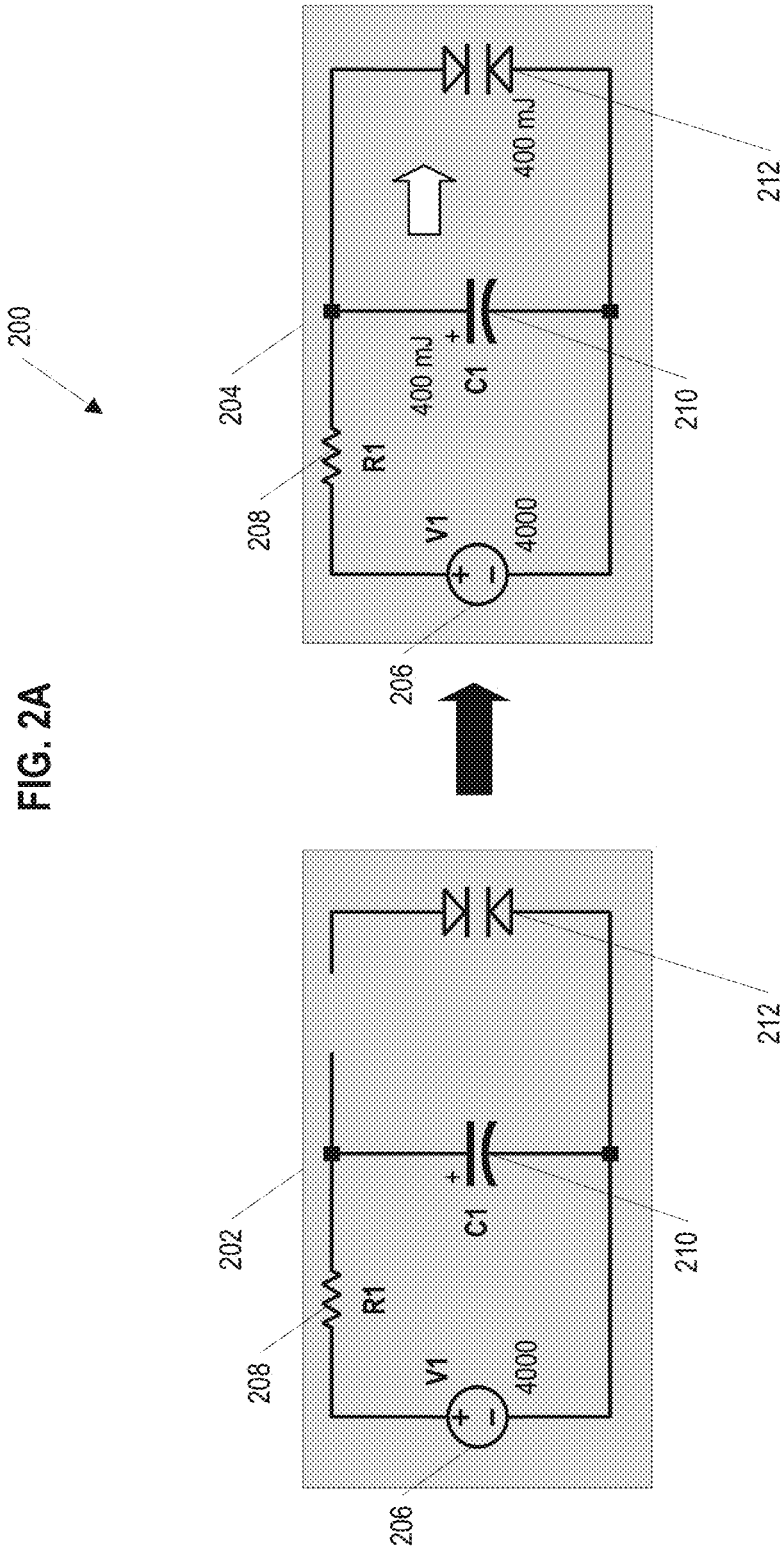
FIGS. 2A and 2B illustrate exemplary pulse generator configurations, according to examples of the disclosure.
Figure 2B:
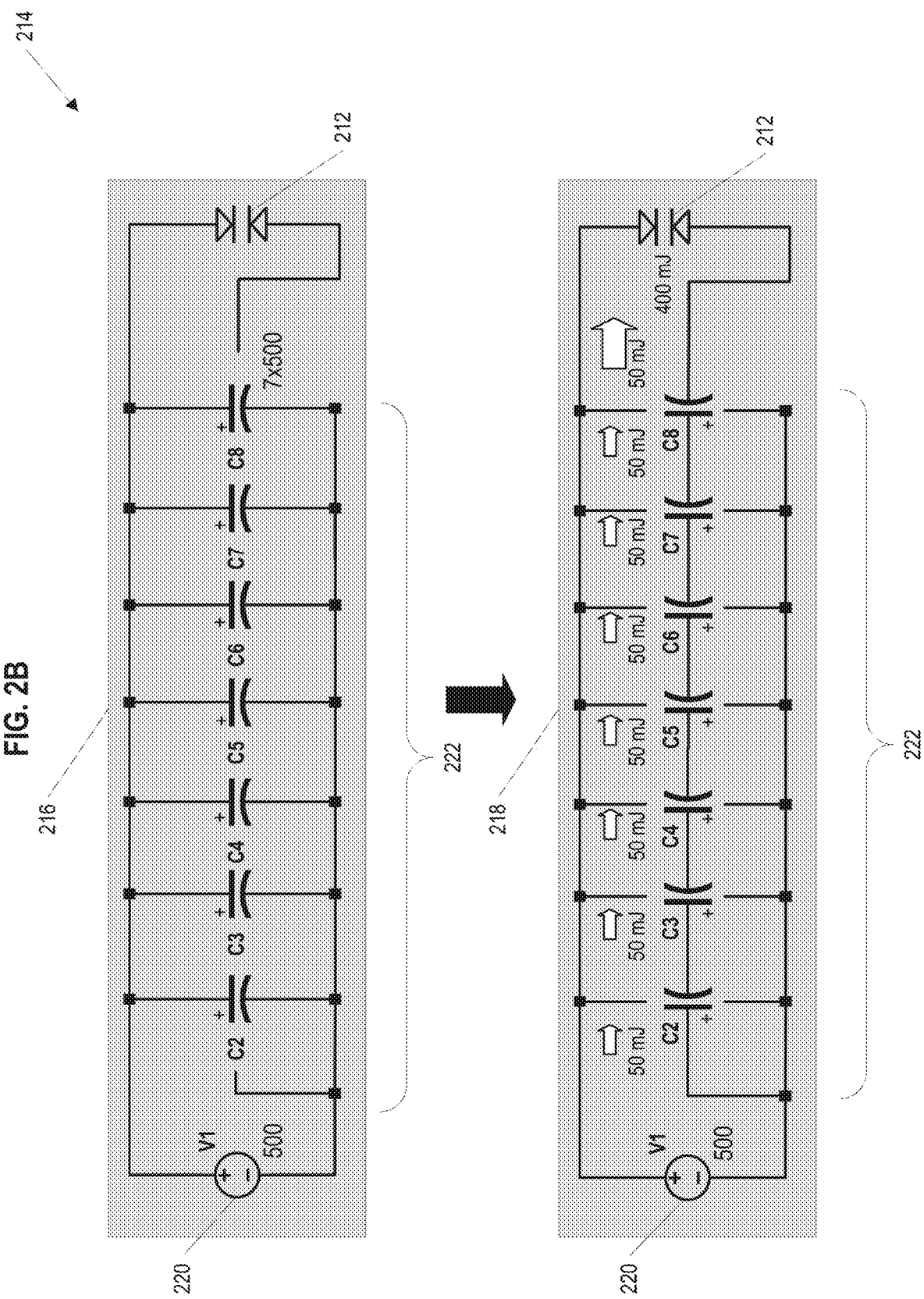

FIGS. 2A and 2B illustrate pulse generator configurations that use the same voltage source to generate the voltages for bubble generation and arc generation. The pulse generators 200 and 214 of FIGS. 2A and 2B, respectively, can be configured to generate both a bubble and an arc at electrodes of a shock wave generator. The pulse generator 200 of FIG. 2A can operate in a charging mode 202, wherein the voltage source 206 (labeled as V1 in the figure) can charge a capacitor 210 (labeled as C1 in the figure) through a resistor 208 (labeled as R1 in the figure). In a discharge mode 204, the electrodes 212 can be selectively electrically coupled to the capacitor 210 by, e.g., closing a switch (not shown), thereby causing the energy stored in the capacitor (e.g., in the form of accumulated electrical charge) to discharge onto the electrodes 212. The electrodes 212 can be electrically coupled to the capacitor 210 via a variable resistor (not shown) that can be used to limit the amount of current supplied by the capacitor 210 to the electrodes 212. The amount of current can be adjusted based on whether the catheter system is generating a bubble or generating an arc. For instance, to prime an aqueous environment and/or generate a bubble, the resistance of the variable resistor can be set relatively high such that a smaller potential difference between the electrodes 212 is generated. When the bubble has grown, to generate an arc, the variable resistor can have its resistance lowered to near zero, thereby allowing the full charge stored at the capacitor 210 to be discharged onto the electrodes 212. The electrical arc at the electrodes 212 can cause the shock wave catheter system to generate a shock wave. Additional details of bubble generation and arc generation using the same voltage source are provided in U.S. Pat. No. 9,138,249, which is incorporated by reference.

The pulse generator 214 of FIG. 2B can operate in substantially the same manner as the pulse generator 200 of FIG. 2A described above. The pulse generator 214 of FIG. 2B can be configured as a Marx generator. During the charging mode 216, a voltage source 220 (labeled as V1 in the figure) can charge a plurality of capacitors 222 that are coupled to the voltage source 220 in parallel. In one or more examples, when the circuit is operated in the charging mode 216, the electrodes 212 can be decoupled from the rest of the circuit such that the capacitors 222 charge without discharging any of their energy onto the electrodes 212. During the discharge mode 218, the capacitors 222 can be coupled in series with one another thereby allowing for a high voltage pulse to be discharged at the electrodes 212, which are also electrically coupled to the capacitors 222. Similar to the example system 200 of FIG. 2A, the electrodes 212 can be electrically coupled to the capacitors 222 via a variable resistor (not shown) that can be used to limit the amount of current supplied by the capacitors 222 to the electrodes 212. For instance, to prime an aqueous environment and/or generate a bubble, the resistance of the variable resistor can be set relatively high so as to generate a smaller potential difference between the electrodes 212. When the bubble has grown, to generate an electrical arc, the variable resistor can have its resistance lowered to near zero, thereby allowing the full charge stored at capacitors 222 to be discharged onto the electrodes 212, which in turn can cause the shock wave catheter system to generate a shock wave. Additional details of Marx generators are provided in U.S. Pat. No. 7,855,904, which is incorporated by reference.

The use of the same power source (the capacitor 210 and voltage source 206 in system 200 of FIG. 2A, or the set of capacitors 222 and voltage source 220 in system 214 of FIG. 2B) to supply both the voltage needed to generate a bubble and the voltage needed to generate an electrical arc can present some disadvantages. For instance, by sharing a single voltage source between the bubble generation mode of operation and the arc generation mode, the pulse generator is not independently controllable; generating the bubble and generating the arc are dependent processes. Furthermore, using a single voltage source can require that the voltage source be large enough to support both bubble generation and arc generation modes, since a portion of the energy generated by the voltage source must be discharged to grow a bubble, but the capacitors must also preserve ample energy to generate an electrical arc. The variable resistor used to limit the amount of charge provided to the electrodes during bubble generation mode may convert some of the energy to heat, wasting some of the energy generated by the single voltage source. A voltage source used for both bubble generation and arc generation may have to be larger than otherwise necessary in order to account for these inefficiencies.

In one or more examples of the present disclosure, a pulse generator that utilizes separate bubble generation and arc generation voltage sources may provide overall benefits to the pulse generator that can mitigate the inefficiencies described above. By utilizing separate voltage sources, the bubble generation voltage source can be independently controlled from the arc generation voltage source. This can lead to more efficient use of each voltage source since, unlike a single voltage source system, energy is not wasted in a resistor that has to be used to limit the current being applied to the electrodes during the bubble generation mode of operation. However, configuring the pulse generator with two separate voltage sources can present various challenges. For instance, a pulse generator with two separate voltage sources may need to be configured to offer a high degree of controllability such that the first and second voltage sources can be operated independently from one another, without the operation of one voltage source affecting the operation of the other voltage source.

Figure 3:
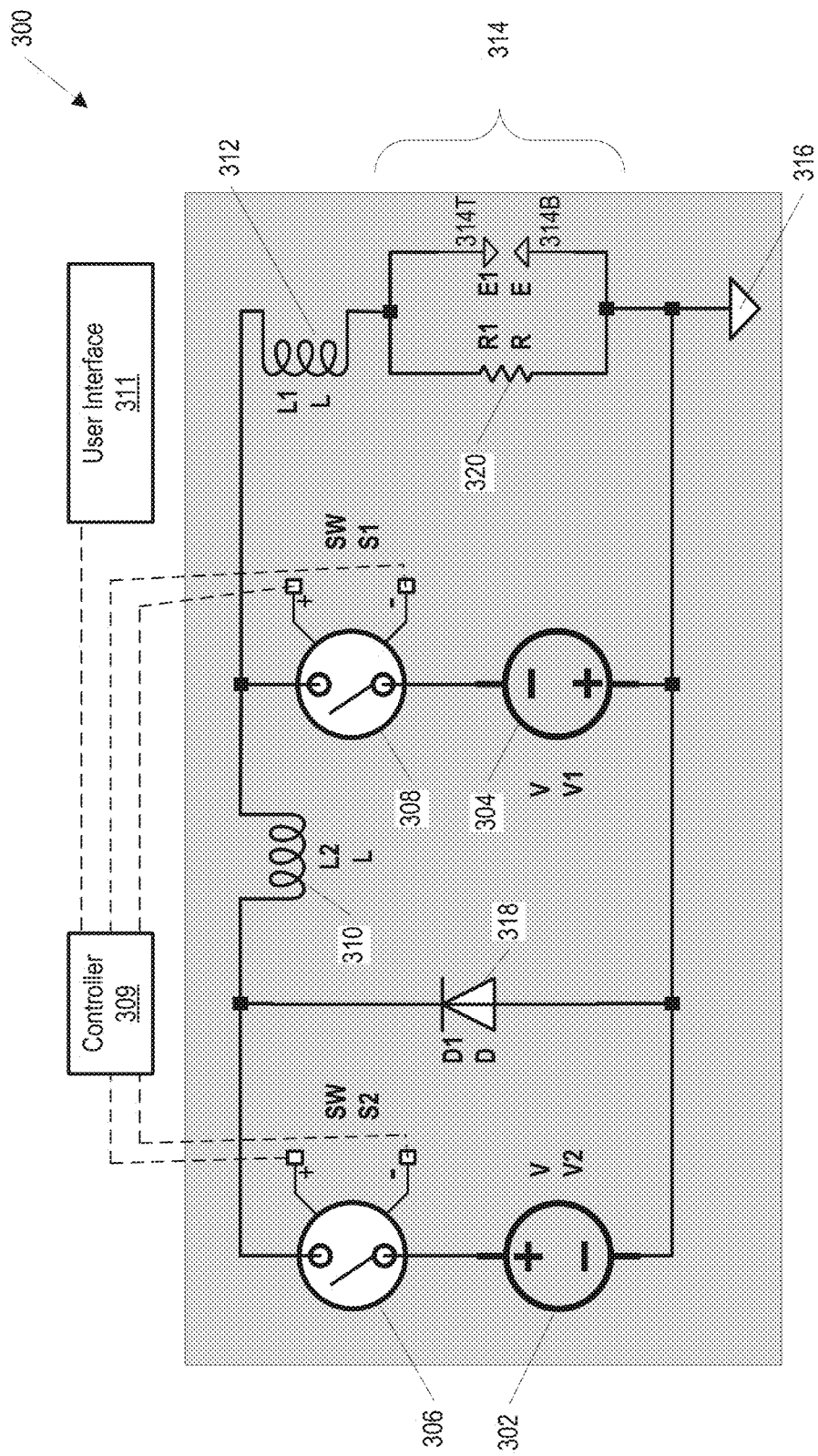
FIG. 3 illustrates an exemplary pulse generator configuration with separate bubble generation and arc generation voltage sources, according to examples of the disclosure.

FIG. 3 illustrates an exemplary pulse generator configuration with separate bubble generation and arc generation voltage sources, according to examples of the disclosure. In one or more examples, the pulse generator 300 of FIG. 3 can include multiple (e.g., two) separate and independently controllable voltage sources 302 and 304 (both coupled to the reference potential 316). The first voltage source, referred to as bubble generation voltage source 302 (labeled as V2 in the figure), can be configured to generate a voltage at electrodes 314 (discussed in further detail below) that can allow for the electrodes 314 to generate a bubble in a fluid surrounding the electrodes. The second voltage source, referred to as arc generation voltage source 304 (labeled as V1 in the figure), can be configured to generate a voltage at electrodes 314 that can allow for the electrodes 314 to generate an electric arc in a formed bubble that may generate a shock wave similar to the manner described above. In one or more examples, the arc generation voltage source 304 can be implemented as a Marx generator (similar to the example described above with respect to FIG. 2B). Additionally or alternatively, the arc generation voltage source 304 can be implemented as a cap charger (similar to the example described above with respect to FIG. 2A).

In one or more examples, the bubble generation voltage source 302 can generate a voltage that is less than the voltage generated by arc generation voltage source 304. For instance, in one or more examples, the bubble generation voltage source 302 can generate a voltage in the range of fifty to two hundred fifty volts (50-250 V), and the arc generation voltage source 304 can generate a voltage in the range of two thousand to ten thousand volts (2,000-10,000 V), inclusive of increments or gradients of voltages within each of these ranges. The voltage generated may be based on one or more factors, such as application, bubble size, etc. For example, the voltage generated may be based on the number, size, properties, etc. of electrodes in the catheter system, where a certain amount of energy may be needed in order to form a bubble around the electrodes. As another non-limiting example, the time that the bubble generation voltage source 302 and/or arc generation voltage source 304 are on and the energy generated may be based on bubble size. The bubble size may be such that one bubble fills the hole of a shock wave generator 106, for example.

In one or more examples, the pulse generator 300 of FIG. 3 can include one or more separation components that are configured to electrically separate the bubble generation voltage source 302 from the arc generation voltage source 304. For instance, in one or more examples, the separation components can include an inductor 310 and a diode 318. In one or more examples, the inductor 310 can be configured to provide separation between the bubble generation voltage source 302 and the arc generation voltage source 304. Similarly, diode 318 can serve as a protection diode that can provide a current path for the arc generation voltage source 304 and protect bubble generation voltage source 302 from the negative voltage associated with the operation of the arc generation voltage source 304.

In one or more examples, one or more (e.g., each) of the bubble generation voltage source 302 and the arc generation voltage source 304 can be coupled to a switch 306 and a switch 308, respectively, that are independently controllable (described in detail below). When closed, switch 306 can be configured to selectively electrically couple bubble generation voltage source 302 to the one or more electrodes 314. Similarly, when closed, switch 308 can be configured to selectively electrically couple arc generation voltage source 304 to the one or more electrodes 314. In one or more examples, switches 306 and 308 can be independently closed and open by one or more controllers 309 that are coupled to the inputs of the switches. In one or more examples, the switches 306 and 308 can be controlled by common controller, or alternatively, by separate controllers. Additionally, switches 306 and 308 can be implemented as insulated bi-polar gate (IGBT) switches, Metal Oxide Semiconductor Field Effect Transistor (MOSFET) switches, or any other suitable switch types known in the art. In one or more examples, the one or more controllers 309 used to control the switch can be configured to receive an external input and, based on the received input, control the switches 306 and 308 to generate shock waves. Examples of the external inputs to the controller can include receiving an indication that a mechanical or electronic button of a user interface 311 has been pushed by a user of the device. In response to the indication that the mechanical or electronic button has been pushed, the controller(s) 309 can transmit a signal to each of the switches 306 and 308 so as to close or open the switches. As will be described in further detail below, upon a determination that a user of the device has pushed a mechanical or electronic button (indicating that they wish to have the system generate one or more shock waves), the controller(s) 309 can control the switches in an ordered manner so as to cause a shock wave to be generated and can continue generating shock waves at a pre-determined interval until the user releases the mechanical or electronic button.

Note that in FIG. 3, inductor 312 represents the inductance of the wire that couples the pulse generator components (described above) to the electrodes 314, and resistor 320 represents the initial resistance of the fluids around the electrodes 314. The inductor 312 and the resistor 320 are not implemented as actual components in the pulse generator, but instead represent effects caused by the wiring associated with the pulse generator, as well as the fluid surrounding the electrodes 314.

The pulse generator 300 can be configured to operate in a plurality of modes. For example, in a bubble generation mode, the bubble generation voltage source 302 is electrically coupled to the electrodes 314, and generates and applies a voltage at (including across) the electrodes 314 to induce electrolysis in the fluid surrounding the electrodes 314. The pulse generator, upon determining that a bubble has formed (described in detail below) can then operate in an arc generation mode. In the arc generation mode, the arc generation voltage source 304 can be electrically coupled to the electrodes 314, and generates and applies a voltage at (including across) the electrodes 314 to generate an electrical arc at the electrodes 314.

Figure 4:
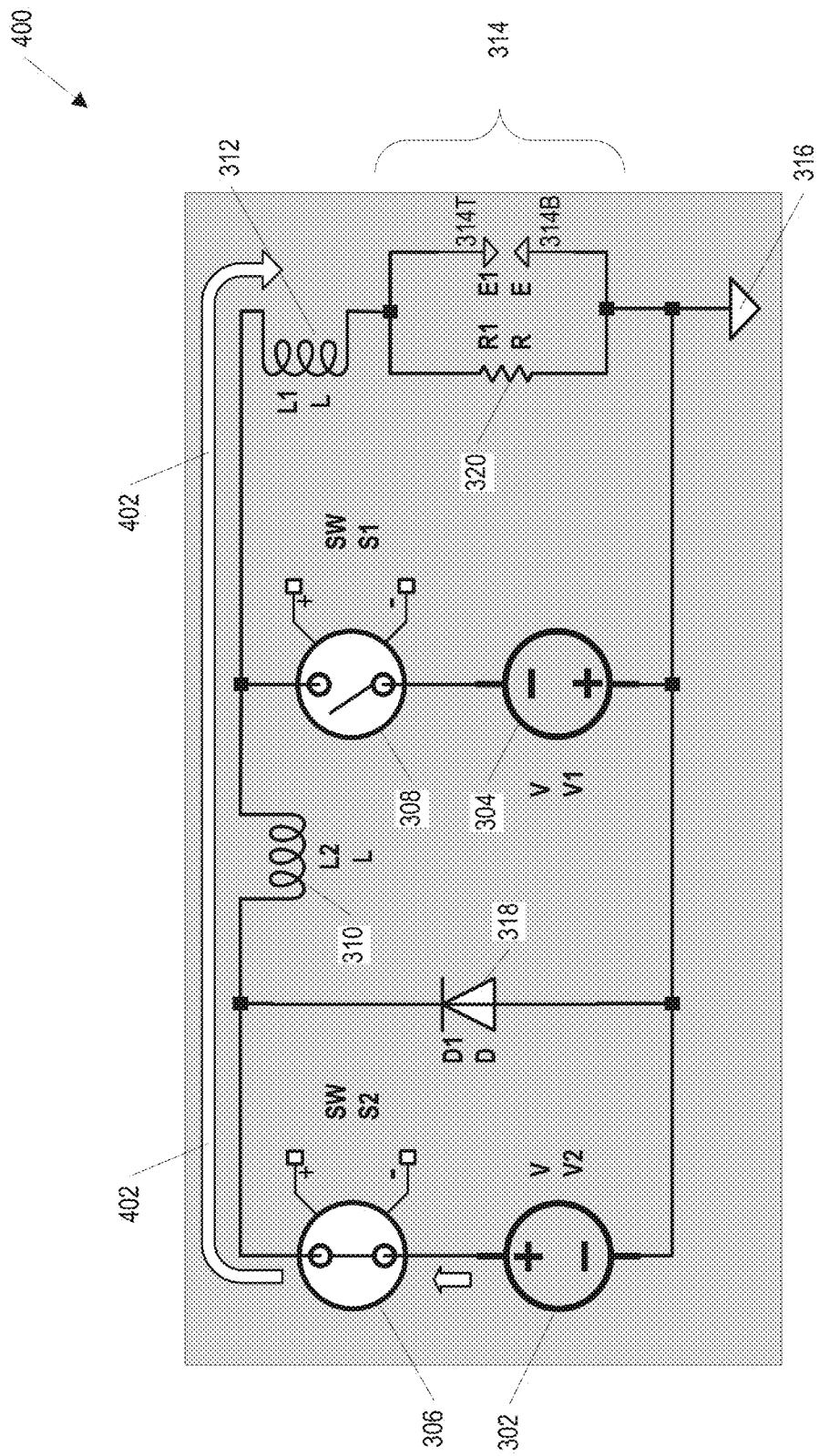
FIG. 4 illustrates an exemplary pulse generator configuration when the pulse generator is operating in a bubble generation operation mode, according to examples of the disclosure.

FIG. 4 illustrates an exemplary pulse generator configuration when the pulse generator is operating in a bubble generation mode, according to examples of the disclosure. In one or more examples, during bubble generation mode, the bubble generation voltage 302 can be electrically coupled to the electrodes 314 by closing the switch 306. Also, during bubble generation mode, the switch 308 (associated with the arc generation voltage source 304) can remain open such that the arc generation voltage source 304 is electrically decoupled from the electrodes 314, thereby not providing any current of its own to the electrodes 314. As illustrated in FIG. 4, when operating in bubble generation mode, closing the switch 306 generates a current pathway 402, allowing current from the bubble generation voltage source 302 to reach the electrodes 314.

In one or more examples, the current along the current pathway 402 can flow through inductor 312 before reaching the electrode 314. In one or more examples, in bubble generation mode, the bubble generation voltage source 302 can be on for a duration such that the initially high impedance of inductor 312 is lowered to a low value, where it acts as a wire that allows current to flow to the electrodes 314.

The bubble generation mode is configured to prime an aqueous environment and/or generate one or more bubbles at the electrodes 314 when surrounded by a fluid (e.g., saline). In one or more examples, generating a bubble is a prerequisite for generating an electrical arc, which can generate a shock wave. Without a sufficiently large bubble, the arc generating voltage source 304 may not be able to generate an arc despite its high voltage. In one or more examples, the bubble generation mode can be terminated based on the size of the bubble. Examples of the disclosure include determining that the size of a bubble meets a certain threshold size, and then terminating the bubble generation mode. In one or more examples, the determination of the bubble size relative to the threshold size can comprise monitoring the amount of time the bubble generation mode has been active and terminating the bubble generation mode once a threshold amount of time has passed.

Additionally or alternatively, the size of the bubble may be determined through the use of a feedback loop that can measure the amount of current, along current pathway 402, that is being delivered to the electrodes 314. The bubble generation mode can be terminated once the measured amount of current meets a threshold amount of current. In one or more examples, the bubble generation mode can be terminated when the current delivered to the electrodes 314 is below one hundred microampere (<100 μA). In one or more examples, terminating the bubble generation mode can include opening switch 306 to electrically decouple the bubble generation voltage source 302 from the electrodes 314. Additionally or alternatively, terminating the bubble generation mode can include initiating the arc generation mode including, but not limited to, leaving the bubble generation voltage source 302 electrically coupled to the electrodes 314 via keeping switch 306 closed.

Figure 5:
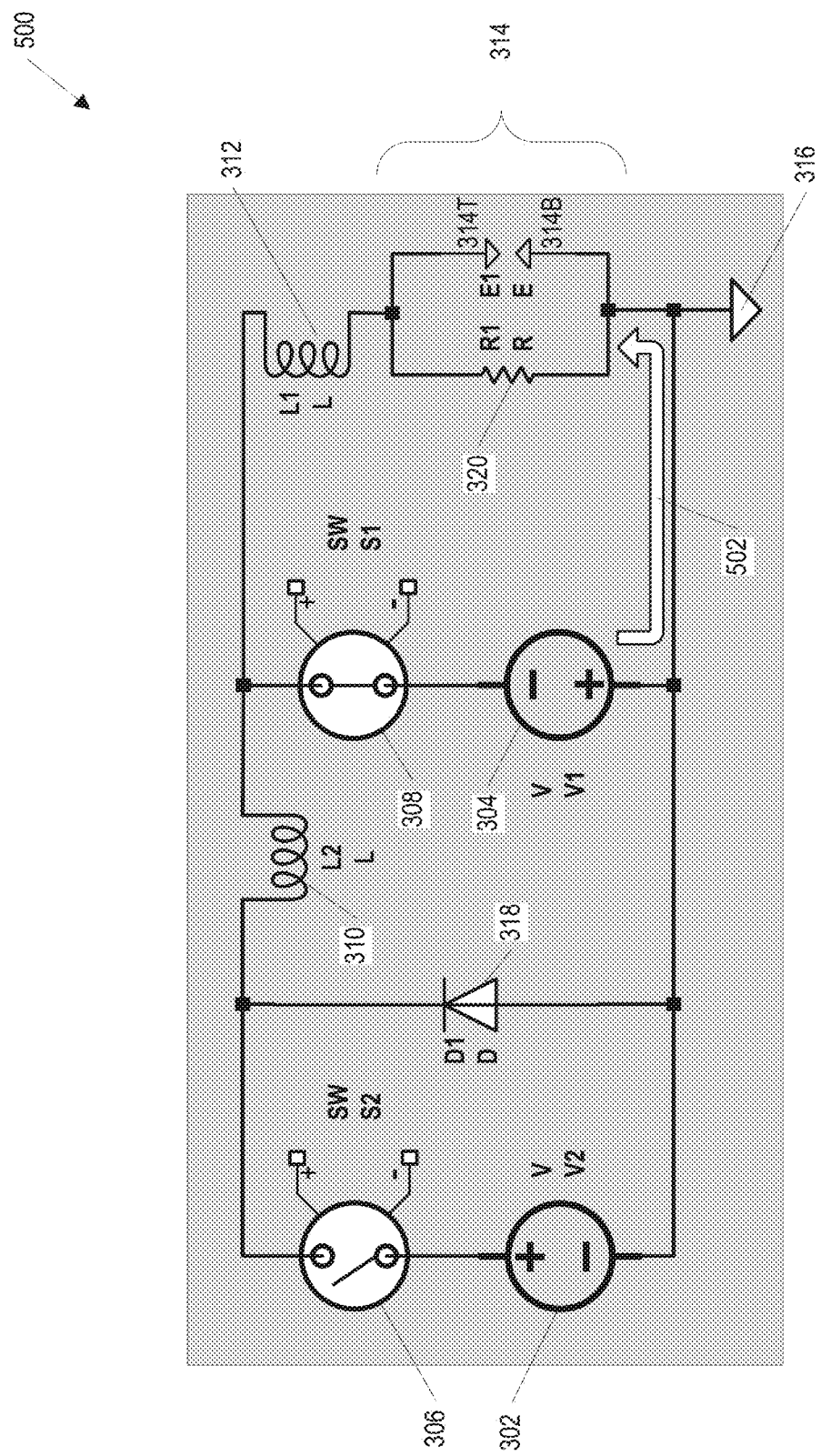
FIG. 5 illustrates an exemplary pulse generator configuration when the pulse generator is operating in an arc generation mode, according to examples of the disclosure.

FIG. 5 illustrates an exemplary pulse generator configuration when the pulse generator is operating in an arc generation mode, according to examples of the disclosure. In one or more examples, the arc generation mode of the pulse generator can be initiated by closing switch 308, thereby electrically coupling the arc generation voltage source 304 with the electrodes 314. In one or more examples, the switch 306 can remain closed during the arc generation mode, causing the bubble generation voltage source 302 to also be electrically coupled to the electrodes 314. Since the bubble generation voltage source 302 is independently controllable from the arc generation voltage source 304, switch 306 can be opened at any point during the arc generation mode including at any time during the arc generation mode or even when the arc generation mode is terminated.

In one or more examples, closing switch 308 at the initialization of the arc generation mode as described can generate a current along current pathway 502 from the arc generation voltage source 304 to the electrodes 314. The impedance of the inductor 310 may restrict the current from the arc generation source 304, reducing or preventing current flow towards the bubble generation voltage source 302, thereby electrically separating the arc generation voltage source 304 from the bubble generation voltage source 302. Additionally or alternatively, a diode or other electronic component can be used to restrict current flow from the arc generation voltage source 304 to the bubble generation voltage source 302.

In one or more examples, and as illustrated in FIGS. 3, 4, and 5, the arc generation voltage source 304 can be arranged in the pulse generator 500 such that its polarity is opposite that of the bubble generation voltage source 302 (opposite polarity arrangement). Arranging the arc generation voltage source 304 such that its polarity is opposite to that of the polarity of the bubble generation voltage source 302 can provide some advantages. For instance, the opposite polarity arrangement can allow for diode 318 to have a lower break down voltage than the same polarity arrangement, since the diode 318 may need to withstand the high voltage being generated by the arc generation voltage source 304 in addition to withstanding the voltage generated by the bubble generation voltage 302. Additionally, by arranging the arc generation voltage source 304 so that it is of opposite polarity to the bubble generation voltage source 302, current can reach the electrodes 314 from the opposite direction. In one or more examples, during the bubble generation mode, the current can reach the top electrode 314T (with respect to the orientation of the figure), as shown in FIG. 3. During the arc generation mode, the current can reach the bottom electrode 314B. Allowing electrons to be inserted from different ends can preserve the life of the electrodes 314. Alternatively, the arc generation voltage source 304 can be arranged to have the same polarity as the bubble generation voltage source 302 same (polarity arrangement, not shown in the figure).

In one or more examples, the arc generation mode can be terminated when it has been determined that the amount of current delivered to electrodes 314 meets a threshold amount of current. In some examples, the threshold amount of current can be the current needed to generate an electrical arc at the electrodes 314. The system can determine that the threshold amount of current has been delivered to the electrodes 314 based on, e.g., a threshold amount of time passing from the initialization of the arc generation mode (e.g., when switch 308 has been closed) before opening switch 308 to terminate the arc generation mode. Additionally or alternatively, the arc generation mode can be terminated based on measuring the amount of current flowing via current pathway 502 from the arc generation voltage source 304 to the electrodes 314, and determining that a threshold amount of current has been delivered to the electrodes 314. For example, if the current is measured to be at or above a minimum threshold of fifty amperes (≥50 A), this can be taken as an indicator that an arc has formed and further delivery of current can be terminated for the given cycle of arc generation.

In one or more examples, the timing relationships between the bubble generation mode and the arc generation mode can be controlled by controlling the switches. The catheter system can operate in bubble generation mode for a longer period of time than in the arc generation mode, and as such, the switch 306 can be closed for longer period of time than the switch 308. This can be because it may take a longer time to form a bubble than it can be to generate an arc to thereby generate a shock wave.

Figure 6:
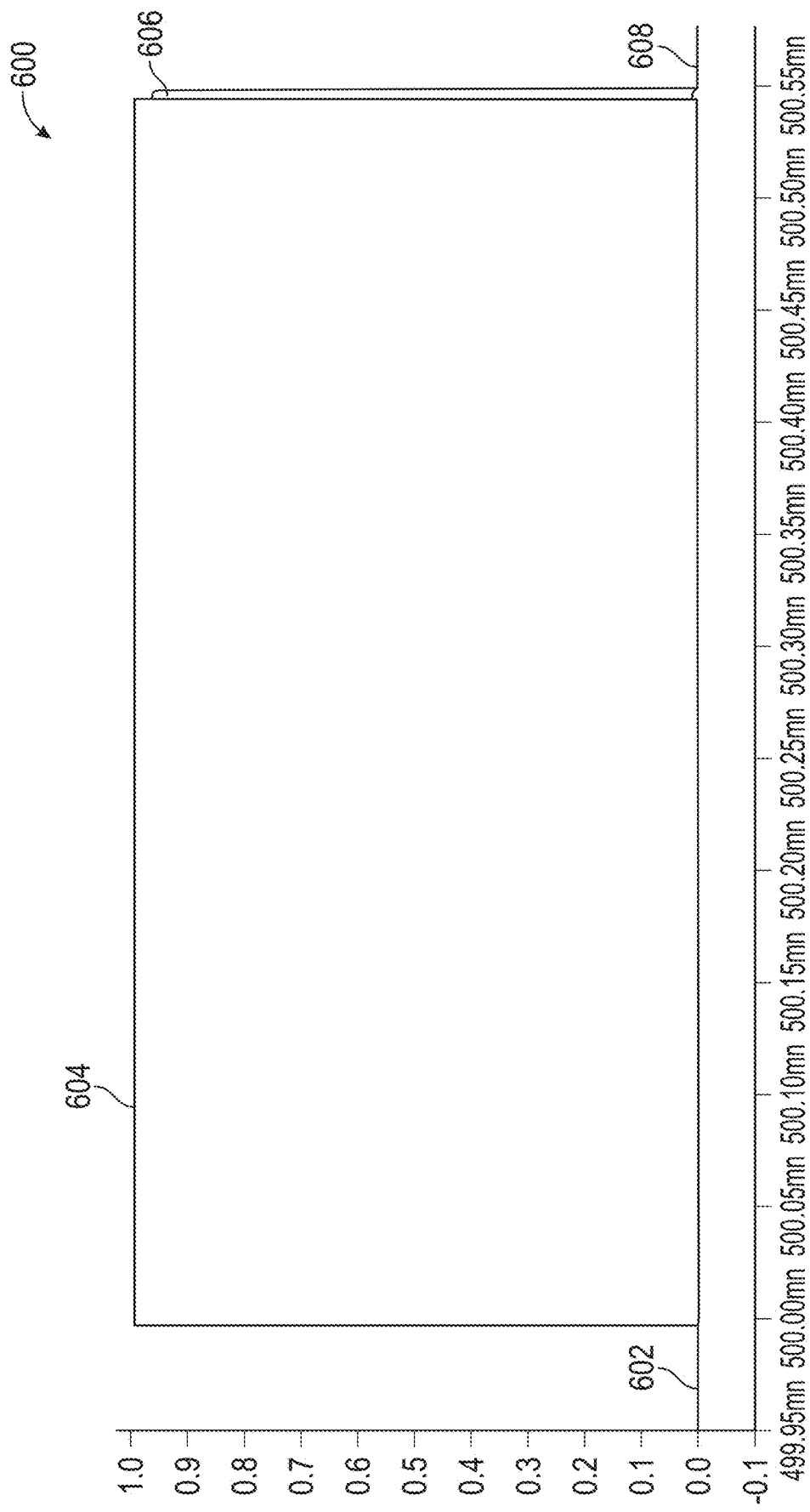
FIG. 6 illustrates an exemplary switch timing diagram for a pulse generator with separated bubble generation and arc generation power sources, according to examples of the disclosure.

FIG. 6 illustrates an exemplary switch timing diagram for a pulse generator with separated bubble generation and arc generation voltage sources, according to examples of the disclosure. In one or more examples, the timing diagram 600 can represent the timing relationships between the bubble generation mode and the arc generation mode, and specifically the timing relationships between the various switches used to initiate each mode, as described above. In one or more examples, the pulse generator described above with respect to FIGS. 3-5 can operate in an initialization mode 602 such that both switches 306 and 308 are open and the electrodes 314 are not receiving any current or voltage from the bubble generation voltage source 302 or the arc generation voltage source 304.

In one or more examples, the pulse generator can operate in the bubble generation mode 604 by closing the switch 306 (shown in the figure as a change from low to high), electrically coupling the bubble generation voltage source 302 with the electrodes 314. In one or more examples, the arc generation mode 606 can be initialized by closing the switch 308 (shown in the figure as a change from low to high), electrically coupling the arc generation voltage source 304 with the electrodes 314. In one or more examples, when switch 308 is closed at the initialization of the arc generation mode 606, switch 306 can be opened (shown in the figure as a change from high to low). Alternatively, switch 306 can be left closed even when switch 308 is closed.

In one or more examples, once it has been determined that a sufficient arc has been generated (as discussed above), switch 308 can be opened (thereby terminating the electrical coupling between the arc generation voltage source 304 and the electrodes 314) and causing the pulse generator to enter a charge mode 608. In charge mode 608, the fluid can be allowed to surround the electrodes, and any capacitors that store charge in the arc generation voltage source 304 can be allowed to charge. In one or more examples, during the charge mode 608, both switches 306 and 308 can be opened. In one or more examples, if switch 306 has not already been opened during arc generation mode 606, then it can be opened when the pulse generator enters the charge mode 608. Furthermore, the charge mode 608, with a suitable combination of electrode material and metal ions present in the fluid (e.g., saline solution), can be used to plate the electrodes with fresh material, counteracting any damage to the electrodes incurred during the arc generation mode 606.

As demonstrated by the timing diagram 600 of FIG. 6, the bubble generation mode 604 can be longer than the arc generation mode 606, meaning that switch 306 can be closed for a longer period of time than switch 308 and/or the bubble generation voltage source 302 may be on for a longer period of time than the arc generation voltage source 304. By separating the voltage sources (e.g., bubble generation voltage source 302 separate from an arc generation source 304), the timing of the pulse generator can be made more efficient since the operation of the switches do not have to be coordinated.

Figure 7:
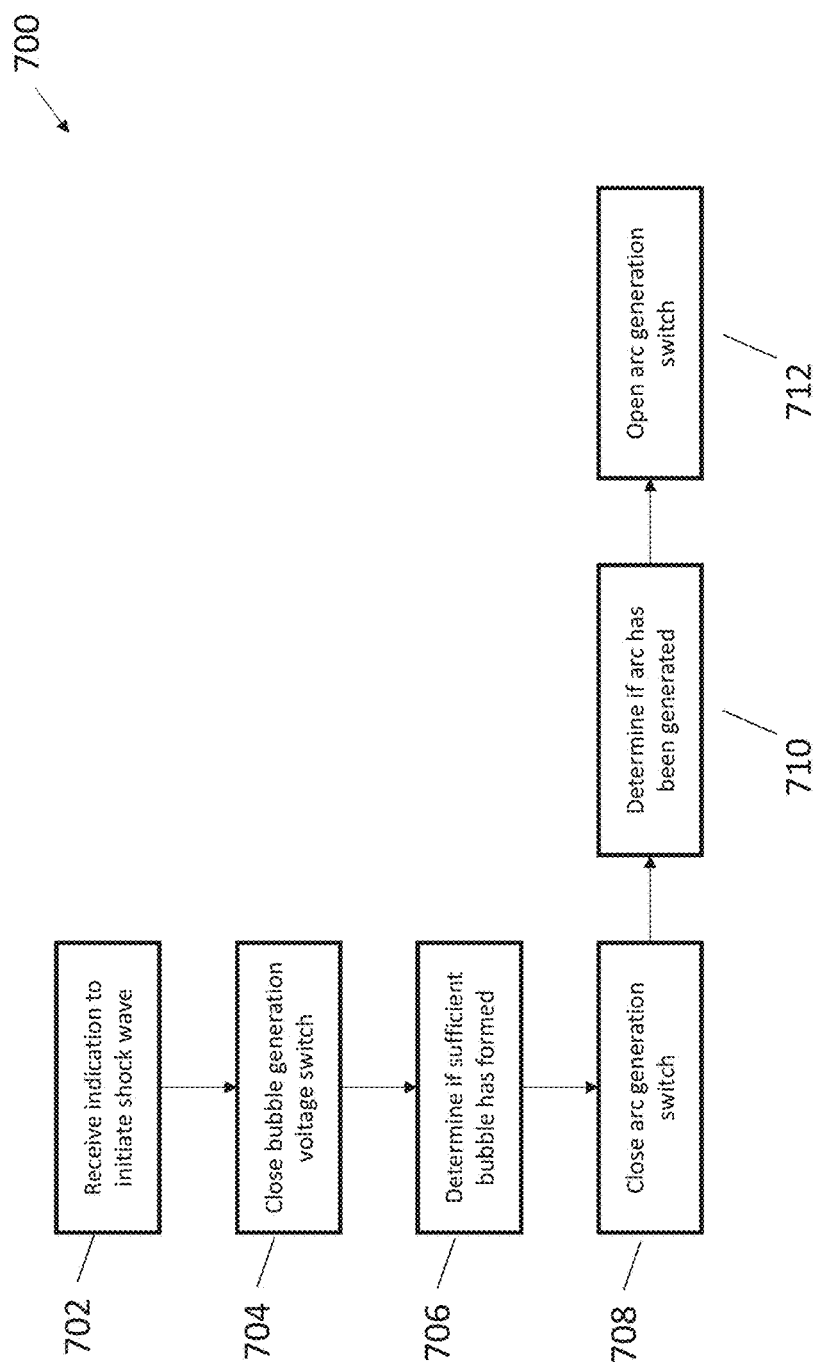
FIG. 7 illustrates an exemplary process for operating a pulse generator with separate bubble generation and arc generation voltage sources, according to examples of the disclosure.

FIG. 7 illustrates an exemplary process for operating a pulse generator with separate bubble generation and arc generation voltage sources, according to examples of the disclosure. In one or more examples, process 700 can begin at step 702, where an indication (such as a determination that user has pushed a button) can be received. Once the indication has been received at step 702, the process 700 can move to step 704, where the one or more controllers 309 of the catheter system operate to close the switch 306 (bubble generation voltage switch), initiating the bubble generation mode of the pulse generator. Once the switch 306 has been closed at step 704, the process 700 can move to step 706, where a determination can be made as to whether a sufficient bubble (e.g., the size of the bubble meets a threshold size) has been formed in the fluid, according to the examples described above.

In one or more examples, once a determination has been made at step 706 that a bubble of sufficient, threshold size has been grown, the process 700 can move to step 708, where the arc generation switch 308 can be closed to initiate the arc generation mode of the pulse generator. Once the switch 308 has been closed at step 708, the process 700 can move to step 710, where a determination can be made as to whether an arc has been generated in accordance with the examples described above. Once a determination has been made at step 710 that an arc has been generated, the process moves to step 712, where the arc generation switch 308 is opened. Additionally, at step 712, the bubble generation switch can be opened (if it has not already been opened) to thereby operate the pulse generator in the charge mode described above.

In one or more examples, the process 700 can repeated so long as the indication to initiate a shock wave is present. In one or more examples, the process 700 can repeat itself so long as the mechanical button pushed by a user of the shock wave catheter system engages the switch. In one or more examples, the process 700 can repeat at a frequency of 1 Hz so long as the user pushes the mechanical button, generating a shock wave at a frequency of once every second. In some examples, the process 700 can repeat at a frequency of 2 Hz, 3 Hz, 4 Hz, ½ Hz, ¼ Hz, or the like. In further examples, the process 700 can repeat at a rate that is alternatively synchronized to a patient heart beat—in other words, the heart beat of a patient drives the frequency of process and the implementation of the process does not pace the heart.

Although the pulse generator disclosed herein is discussed in the context of a shock wave catheter system, examples of the disclosure include a pulse generator that can be used with other types of medical devices. The properties of the pulse generator, as shown in any one of FIGS. 3-5, may be adjusted based on the medical device. For example, the amount of time that the first switch and/or second switch electrically couples a voltage source to the electrodes, the amount of voltage generated by a voltage source, etc., may be changed. In some examples, the properties of the pulse generator may be changed by changing a program stored in memory and executed by a processor (e.g., controller 309).

In some examples, the pulse generator may be operated for backplating the electrodes, according to examples of the disclosure. The arc generation (discussed above) may cause erosion to the electrodes due to, e.g., current discharge between the electrodes removing material. Erosion of the material reduces the lifetime of the electrodes. Backplating the electrodes can reduce the amount of erosion and/or reverse the amount of material degradation on the surfaces of the electrodes by causing metal to be deposited on the electrode(s).

Figure 8A:
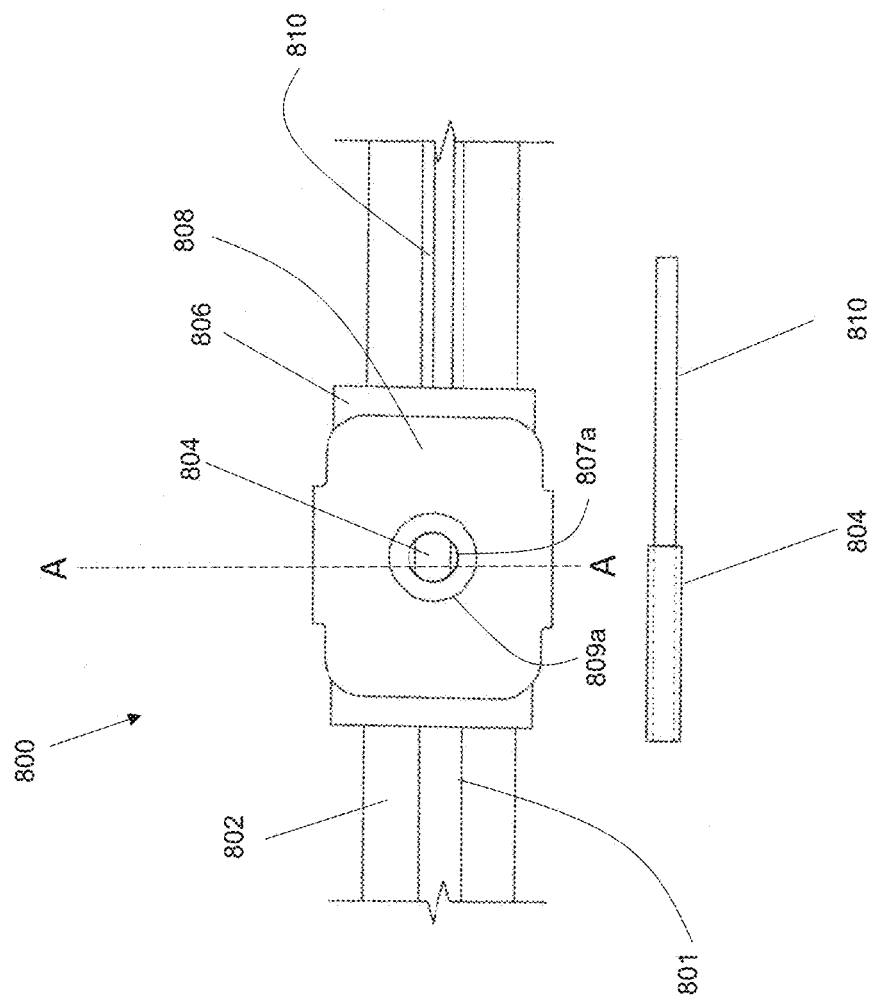
FIG. 8A illustrates a top view of an example electrode assembly, according to examples of the disclosure.

FIG. 8A illustrates a top view of an example electrode assembly 800 comprising a first inner electrode 804, an insulating layer or sheath 806 disposed over the first inner electrode 804 and circumferentially wrapped around an elongate member 802 (e.g., a catheter with a guidewire lumen), and an outer electrode sheath 808 disposed over the insulating sheath 806. The inner electrode 804 and the outer electrode 808 may each be connected to a high voltage pulse generator via a plurality of wires 810 that may be located within a plurality of longitudinal grooves 801 along the outer surface of the elongate member 802 (e.g., a catheter having a guidewire lumen) of the shockwave device. The insulating sheath 806 may have a first opening 807a that is coaxially aligned over the first inner electrode 804, and the outer electrode sheath 808 may have a first opening 809a that is coaxially aligned over the first opening of the insulating sheath. Erosion of the electrodes may occur at the edges of the outer electrode 808 and/or in the corners of the inner electrode 804.

Figure 8B:
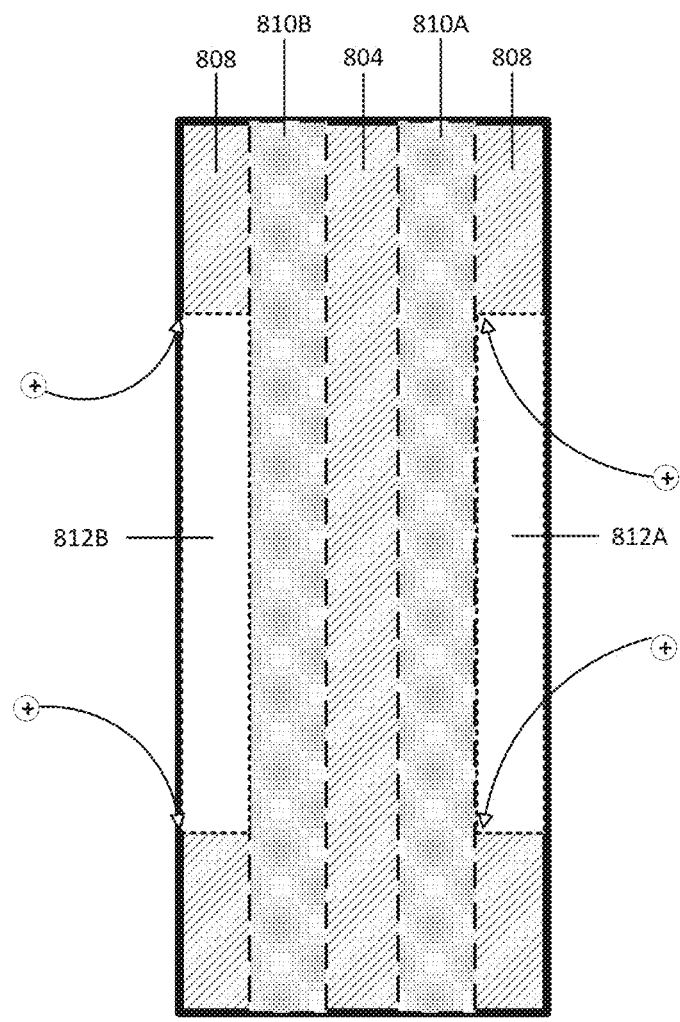

FIGS. 8B and 8C illustrate cross-sectional views taken along A-A of the example electrode assembly 800 of FIG. 8A. FIG. 8A illustrates the electrode assembly 800 when a positive polarity is applied to the backplating operation, and FIG. 8B illustrates the electrode assembly 800 when a negative polarity is applied. A fluid may surround the electrodes 804 and 808, where the fluid may be compatible with the backplating operation. Example fluids may include, but are not limited to, iron salts that are water soluble (e.g., ferrous sulfate solutions), noble metal salts, titanium in salt solution, etc. In some examples, the fluid may comprise two or more biocompatible metals (e.g., silver citrate). In some examples, the fluid is suitable for the backplating operation and bubble generation and additionally does not impede radiographic imaging during IVL procedures. In some examples, one or more parameters (e.g., pH, salt concentrations) of the fluid is adjusted to optimize backplating conditions for the material being plated. Additionally or alternatively, the fluid surrounding the electrodes may comprise a fluid that is compatible with the backplating operation and a fluid that is compatible with the bubble generation. For example, the volume of the fluid surrounding the electrodes may comprise 10-25% of a fluid compatible with backplating and 75-90% of a fluid compatible with bubble generation. In some examples, the fluid is a mixture of one or both of a commercially available biocompatible electroplating solution and a saline solution.

FIG. 9A illustrates an exemplary process for backplating operation when a positive polarity (FIG. 8B) is applied for the backplating operation, according to examples of the disclosure. Process 900 can begin at step 902, where a voltage source (e.g., the bubble generation voltage source 302, the arc generation voltage source 304, or a different voltage source) applies a backplating voltage (e.g., μV) to the electrodes. In some examples, the backplating voltage may be applied across the electrodes. The backplating voltage may be lower than the bubble generation voltage and/or the arc generation voltage. Applying the backplating voltage may generate a spark that jumps from the first wire 810A (of FIG. 8B) across a first spark gap 812A (of FIG. 8B) (step 904). The spark may jump across a second spark gap 812B (of FIG. 8B) (step 906), and then jumps to the second wire 810B (step 908). At step 910, material deposits on the electrode(s).

Figure 9B:
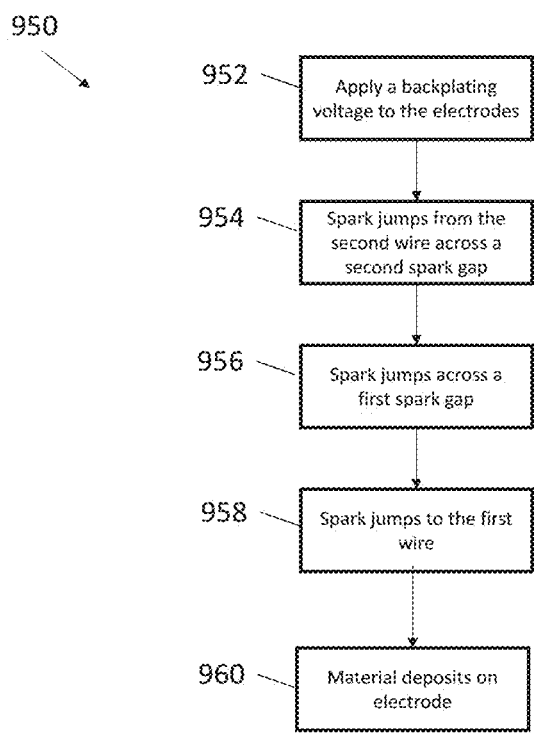
FIG. 9B illustrates an exemplary process for a backplating operation when a negative polarity (FIG. 8C) is applied, according to examples of the disclosure.

In some examples, the backplating operation may deposit metal on both electrodes by switching the polarity of the applied backplating voltage. FIG. 9B illustrates an exemplary process for the backplating operation when a negative polarity (FIG. 8C) is applied, according to examples of the disclosure. Process 950 can begin at step 952, where a voltage source (e.g., the bubble generation voltage source 302, the arc generation voltage source 304, or a different voltage source) applies a backplating voltage to the electrodes. Applying the backplating voltage may generate a spark that jumps from the second wire 810B (of FIG. 8C) across a second spark gap 812B (of FIG. 8C) (step 954). At step 956, the spark may jump to the first spark gap 812A (of FIG. 8C), and at step 958, may jump from the first spark gap 812A to the first wire 810A. At step 960, material deposits on the electrode(s).

Figure 10:
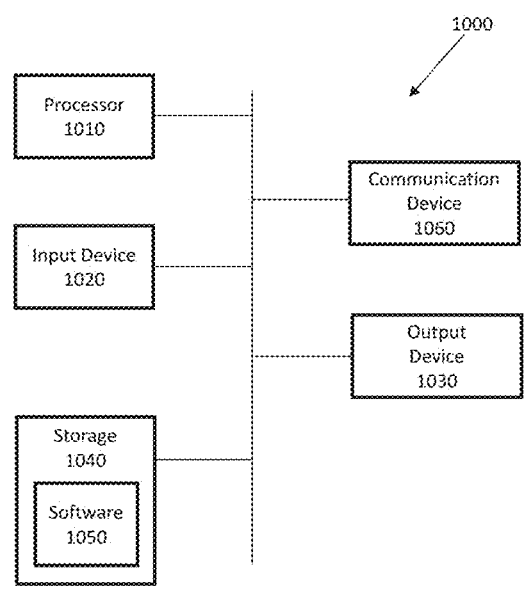
FIG. 10 illustrates an exemplary computing system, according to examples of the disclosure.

FIG. 10 illustrates an example of a computing system 1000, in accordance with some examples of the disclosure. System 1000 can be a client or a server. As shown in FIG. 10, system 1000 can be any suitable type of processor-based system, such as a personal computer, workstation, server, handheld computing device (portable electronic device) such as a phone or tablet, or dedicated device. The system 1000 can include, for example, one or more of input device 1020, output device 1030, one or more processors 1010, storage 1040, and communication device 1060. Input device 1020 and output device 1030 can generally correspond to those described above and can either be connectable or integrated with the computer.

Input device 1020 can be any suitable device that provides input, such as a touch screen, keyboard or keypad, mouse, gesture recognition component of a virtual/augmented reality system, or voice-recognition device. Output device 1030 can be or include any suitable device that provides output, such as a display, touch screen, haptics device, virtual/augmented reality display, or speaker.

Storage 1040 can be any suitable device that provides storage, such as an electrical, magnetic, or optical memory including a RAM, cache, hard drive, removable storage disk, or other non-transitory computer readable medium. Communication device 1060 can include any suitable device capable of transmitting and receiving signals over a network, such as a network interface chip or device. The components of the computing system 1000 can be connected in any suitable manner, such as via a physical bus or wirelessly.

Processor(s) 1010 can be any suitable processor or combination of processors, including any of, or any combination of, a central processing unit (CPU), graphics processing unit (GPU), field programmable gate array (FPGA), programmable system on chip (PSOC), and application-specific integrated circuit (ASIC). Software 1050, which can be stored in storage 1040 and executed by one or more processors 1010, can include, for example, the programming that embodies the functionality or portions of the functionality of the present disclosure (e.g., as embodied in the devices as described above)

Software 1050 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1040, that can contain or store programming for use by or in connection with an instruction execution system, apparatus, or device.

Software 1050 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1000 can implement any operating system suitable for operating on the network. Software 1050 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated. For the purpose of clarity and a concise description, features are described herein as part of the same or separate embodiments; however, it will be appreciated that the scope of the disclosure includes embodiments having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

It should be noted that the elements and features of the example catheters illustrated throughout this specification and drawings may be rearranged, recombined, and modified without departing from the present invention. For instance, while this specification and drawings describe and illustrate several example electrode assemblies, the present disclosure is intended to include catheters having a variety of electrode configurations. Further, the number, placement, and spacing of the electrode pairs and assemblies can modified without departing from the subject invention.

It will be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A method for generating a shock wave in a shock wave catheter system, the method comprising:
    applying a first voltage, using a first voltage source, to one or more electrodes of the shock wave catheter system to prime an aqueous environment or generate one or more bubbles in a fluid surrounding the one or more electrodes; and
    applying a second voltage, using a second voltage source, to the one or more electrodes to generate an electrical arc at the one or more electrodes,
    wherein the first voltage source and the second voltage source are independently controllable; and
    applying a third voltage to the one or more electrodes of the shock wave catheter system to cause metal to be deposited on the one or more electrodes, wherein the applied third voltage is less than the applied first voltage.

2. The method of claim 1, further comprising:
    selectively electrically coupling or decoupling the first voltage source or the second voltage source with the one or more electrodes.

3. The method of claim 1, further comprising:
    electrically separating the first voltage source from the second voltage source.

4. The method of claim 3, wherein the electrically separating comprises restricting current flow between the first voltage source and the second voltage source.

5. The method of claim 1, further comprising:
    receiving an external input corresponding to a user operating a button; and
    generating one or more signals to control a first switch or a second switch of the shock wave catheter system based on the external input.

6. The method of claim 1, further comprising:
    operating the shock wave catheter system in a bubble generation mode, comprising:
        closing a first switch to electrically couple the first voltage source with the one or more electrodes; and
        opening a second switch to electrically decouple the second voltage source from the one or more electrodes.

7. The method of claim 1, further comprising:
    operating the shock wave catheter system in an arc generation mode, comprising:
        closing a second switch to electrically couple the second voltage source with the one or more electrodes.

8. The method of claim 1, further comprising:
    determining whether a bubble has been formed at the one or more electrodes; and
    in accordance with the bubble having been formed, operating the shock wave catheter system in an arc generation mode.

9. The method of claim 8, wherein the determining whether a bubble has been formed comprises determining whether the shock wave catheter system has operated in a bubble generation mode for a threshold amount of time.

10. The method of claim 8, wherein the determining whether a bubble has been formed comprises determining whether an amount of current flowing from the first voltage source to the one or more electrodes meets a threshold amount of current.

11. The method of claim 10, wherein the amount of current flowing meeting the threshold amount of current comprises the amount of current flowing being less than 100 uA.

12. The method of claim 1, further comprising:
    determining whether an amount of current flowing from the second voltage source to the one or more electrodes meets a threshold amount of current; and
    in accordance with the amount of current flowing meeting the threshold amount of current, terminating operation of the shock wave catheter system in an arc generation mode.

13. The method of claim 12, wherein the amount of current flowing meeting the threshold amount of current comprises the amount of current flowing being greater than 50 A.

14. The method of claim 1, further comprising:
    operating the shock wave catheter system in a bubble generation mode; and
    operating the shock wave catheter system in an arc generation mode,
    wherein a period of time for operating in the bubble generation mode is longer than a period of time for operating in the arc generation mode.

15. The method of claim 1, wherein the applied first voltage is less than the applied second voltage.

16. The method of claim 1, wherein the applied first voltage is from 50 to 250 volts.

17. The method of claim 1, wherein the applied second voltage is from 2,000 to 10,000 volts.

18. The method of claim 1, wherein the first voltage is applied across the one or more electrodes of the shock wave catheter system.

19. The method of claim 1, wherein the second voltage is applied across the one or more electrodes of the shock wave catheter system.

20. The method of claim 1, wherein the third voltage is applied when the one or more electrodes is surrounded by a second fluid, wherein the second fluid is compatible with a backplating operation.

21. The method of claim 1, wherein the fluid surrounding the one or more electrodes comprises a fluid compatible with backplating and a fluid compatible with bubble generation.

22. The method of claim 21, wherein a volume of the fluid surrounding the one or more electrodes comprises 10-25% of the fluid compatible with backplating and 75-90% of the fluid compatible with bubble generation.

23. The method of claim 1, wherein the one or more electrodes are included in an electrode pair, and the first voltage and the second voltage are applied to electrodes of the electrode pair.

* * * * *